United States Patent
Anderson et al.

(10) Patent No.: US 7,790,684 B2
(45) Date of Patent: Sep. 7, 2010

(54) METHOD OF INHIBITING OSTEOCLAST ACTIVITY

(75) Inventors: Dirk M. Anderson, Port Townsend, WA (US); Laurent J. Galibert, Prevessin Moens (FR)

(73) Assignee: Immunex Corporation, Thousand Oaks, CA (US)

(*) Notice: Subject to any disclaimer, the term of this patent is extended or adjusted under 35 U.S.C. 154(b) by 237 days.

(21) Appl. No.: 12/137,397

(22) Filed: Jun. 11, 2008

(65) Prior Publication Data

US 2009/0004196 A1 Jan. 1, 2009

Related U.S. Application Data

(60) Continuation of application No. 09/705,985, filed on Nov. 3, 2000, now abandoned, which is a continuation of application No. PCT/US99/10588, filed on May 13, 1999, application No. 12/137,397, which is a continuation-in-part of application No. 11/881,911, filed on Jul. 30, 2007, which is a continuation-in-part of application No. 10/405,878, filed on Apr. 1, 2003, now Pat. No. 7,262,274, which is a continuation of application No. 09/871,291, filed on May 30, 2001, now Pat. No. 6,562,948, which is a division of application No. 09/577,800, filed on May 24, 2000, now Pat. No. 6,479,635, which is a continuation of application No. 09/466,496, filed on Dec. 17, 1999, now Pat. No. 6,528,482, which is a continuation of application No. 08/996,139, filed on Dec. 22, 1997, now Pat. No. 6,017,729.

(60) Provisional application No. 60/110,836, filed on Dec. 3, 1998, provisional application No. 60/085,487, filed on May 14, 1998, provisional application No. 60/064,671, filed on Oct. 14, 1997, provisional application No. 60/077,181, filed on Mar. 7, 1997, provisional application No. 60/059,978, filed on Dec. 23, 1996.

(51) Int. Cl.
*A61K 38/17* (2006.01)
*C07K 14/47* (2006.01)
*C07K 14/715* (2006.01)

(52) U.S. Cl. .................. 514/12; 530/350; 530/866

(58) Field of Classification Search .................. None
See application file for complete search history.

(56) References Cited

U.S. PATENT DOCUMENTS

| | | | |
|---|---|---|---|
| 5,843,678 | A | 12/1998 | Boyle |
| 6,015,938 | A | 1/2000 | Boyle et al. |
| 6,017,729 | A | 1/2000 | Anderson et al. |
| 6,087,555 | A | 7/2000 | Dunstan et al. |
| 6,150,090 | A | 11/2000 | Baltimore et al. |
| 6,242,213 | B1 | 6/2001 | Anderson |
| 6,242,586 | B1 | 6/2001 | Gorman et al. |
| 6,271,349 | B1 | 8/2001 | Dougall et al. |
| 6,284,485 | B1 | 9/2001 | Boyle et al. |
| 6,284,728 | B1 | 9/2001 | Boyle et al. |
| 6,284,740 | B1 | 9/2001 | Boyle et al. |
| 6,288,032 | B1 | 9/2001 | Boyle et al. |
| 6,316,408 | B1 | 11/2001 | Boyle |
| 6,369,027 | B1 | 4/2002 | Boyle et al. |
| 6,410,516 | B1 | 6/2002 | Baltimore et al. |
| 6,419,929 | B1 | 7/2002 | Anderson |
| 6,479,635 | B1 | 11/2002 | Anderson et al. |
| 6,525,180 | B1 | 2/2003 | Gorman et al. |
| 6,528,482 | B1 | 3/2003 | Anderson et al. |
| 6,537,763 | B2 | 3/2003 | Dougall et al. |
| 6,562,948 | B2 | 5/2003 | Anderson |
| 6,649,164 | B2 | 11/2003 | Maraskovsky |
| 6,740,522 | B2 | 5/2004 | Anderson |
| 6,838,262 | B1 | 1/2005 | Anderson |
| 7,063,841 | B2 | 6/2006 | Gorman et al. |
| 7,097,834 | B1 | 8/2006 | Boyle |
| 7,262,274 | B2 | 8/2007 | Anderson et al. |
| 2003/0100488 | A1 | 5/2003 | Boyle |
| 2003/0103978 | A1 | 6/2003 | Deshpande et al. |
| 2003/0104485 | A1 | 6/2003 | Boyle |
| 2003/0144480 | A1 | 7/2003 | Gorman et al. |
| 2004/0023313 | A1 | 2/2004 | Boyle et al. |
| 2004/0033535 | A1 | 2/2004 | Boyle et al. |

(Continued)

FOREIGN PATENT DOCUMENTS

EP 0816380 1/1998

(Continued)

OTHER PUBLICATIONS

Oyajobi et al., "Therapeutic efficacy of a soluble receptor activator of nuclear factor κB IgG Fc fusion protein in suppressing bone resorption and hypercalcemia in a model of humoral hypercalcemia of malignancy," Cancer Res 61:2572-2578, 2001.

(Continued)

*Primary Examiner*—David S Romeo
(74) *Attorney, Agent, or Firm*—Scott L. Ausenhus

(57) ABSTRACT

Methods for inhibiting osteoclastogenesis by administering a soluble RANK polypeptide are disclosed. Such methods can be used to treat a variety of different cancers, including bone cancer, multiple myeloma, melanoma, breast cancer, squamous cell carcinoma, lung cancer, prostate cancer, hematologic cancers, head and neck cancer and renal cancer.

10 Claims, No Drawings

U.S. PATENT DOCUMENTS

| | | | |
|---|---|---|---|
| 2005/0003400 | A1 | 1/2005 | Boyle |
| 2005/0089522 | A1 | 4/2005 | Anderson |
| 2006/0246064 | A1 | 11/2006 | Boyle |
| 2008/0009014 | A1 | 1/2008 | Anderson |

FOREIGN PATENT DOCUMENTS

| | | |
|---|---|---|
| EP | 0873998 | 10/1998 |
| EP | 0874045 A1 | 10/1998 |
| EP | 0911342 | 4/1999 |
| EP | 0955372 A2 | 10/1999 |
| WO | WO 93/08207 | 4/1993 |
| WO | WO 94/10308 | 11/1994 |
| WO | WO 95/33051 | 7/1995 |
| WO | WO 96/34095 | 10/1996 |
| WO | WO 96/40918 | 12/1996 |
| WO | WO 97/23614 | 3/1997 |
| WO | WO 98/07840 A1 | 2/1998 |
| WO | WO 98/25958 | 6/1998 |
| WO | WO 98/28423 | 7/1998 |
| WO | WO 98/28424 A2 | 7/1998 |
| WO | WO 98/46751 | 10/1998 |
| WO | WO 98/49305 A1 | 11/1998 |
| WO | WO 98/54201 | 12/1998 |
| WO | WO 99/19468 A1 | 4/1999 |
| WO | WO 99/29865 | 6/1999 |
| WO | WO 99/53942 A1 | 10/1999 |
| WO | WO 99/58674 A2 | 11/1999 |
| WO | WO 99/65449 | 12/1999 |
| WO | WO 99/65495 | 12/1999 |
| WO | WO 01/03719 A2 | 1/2001 |
| WO | WO 01/17543 A2 | 3/2001 |
| WO | WO 01/18203 A1 | 3/2001 |
| WO | WO 01/23549 | 5/2001 |
| WO | WO 01/62932 | 8/2001 |
| WO | WO 02/15846 A2 | 2/2002 |
| WO | WO 03/002713 A2 | 9/2003 |
| WO | WO 03/086289 | 10/2003 |

OTHER PUBLICATIONS

Roodman, "Osteoclast function in Paget's Disease and multiple myeloma," Bone 17(2)(Suppl):57S-61S, 1995.
Anderson et al., "A homologue of the TNF receptor and its ligand enhance T-cell growth and dendritic-cell function," Nature 390:175-179, 1997.
Baker, Stacey J. and Reddy, E. Premkumar, "Transducers of life and death: TNF receptor superfamily and associated proteins," Oncogene, 12(1):1-9, 1996.
Bluemke et al., "Skeletal complications of radiation therapy," Radiographs 1994; 14:111-121.
Castro et al., "15 years experience with helium ion radiotherapy for uveal melanoma," Int J Radiat Oncol Biol Phys 1997; 39(5):989-996 (abstract only).
Darnay et al., J. Biol. Chem. 273(32):20551-20555; 1998.
DiBiase et al., "Palliative irradiation for focally symptomatic metastatic renal cell carcinoma: support for escalation based on a biological model," J Urol 1997; 158(3 Pt 1):746-749 (abstract only).
El-Shirbiny et al., "Technetium-99m-MIBI versus fluorine-18-FDG in diffuse multiple myeloma," J Nuclear Med 1997; 38:1208-1210.
Fisher et al., "Reanalysis and results after 12 years of follow-up in a randomized clinical trial comparing total mastectomy . . . with or without irradiation in the treatment of breast cancer." N Engl J Med 333:1456-1461 (1995).
Forman et al.,"The experience with neutron irradiation in locally advanced adenocarcinoma of the prostate," Semin Urol Oncol 1997; 4:239-243 (abstract only).
Fu, Radiation therapy with 5-fluorouracil in head and neck cancer, Semin Radiat Oncol 1997; 7(4):274-282 (abstract only).
Fuller, K., et al., "TRANCE is necessary and sufficient for osteoblast-mediated activation of bone resorportion in osteoclasts." J. Exp. Med., 188:997-1001 (1998).

Galibert et al., "The involvement of multiple tumor necrosis factor receptor (TNFR)-associated factors in the signaling mechanisms of receptor activator of NF-κB, a member of the TNFR superfamily," J. Biol. Chem. 273(51):34120-34127, 1998.
Guise, Theresa A. and Mundy, Gregory R., "Cancer and bone," Endocrine Reviews 19(1):18-54,1998.
Kodaira et al., "Cloning and characterization of the gene encoding mouse osteoclast differentiation factor," Gene 230:121-127, 1999.
Kwon et al., "cDNA sequences of two inducible T-cell genes," Proc. Natl. Acad. Sci. USA 86:1963, 1989.
Lacey et al., "Osteoprotegerin ligand is a cytokine that regulates osteoclast differentiation and activation," Cell, 93:165-175, 1998.
Mayer e al., "Postoperative radiotherapy in radically resected non-small cell lung cancer." CHEST 112:954-959 (1997).
Monfardini et al., "Recombinant antibodies in bioactive peptide design," JBC 1995; 270:6628-6638.
Nakagawa et al., "RANK is the essential signaling receptor for osteoclast differentiation factor in osteoclastogenesis," Biochem. And Biophys. Res. Comm. 253:395-400, 1998.
Reddi, A. H. "Bone morphogenesis and modeling: soluble signals sculpt osteosomes in the solid state," Cell, 89:159-161 (1997).
Roodman, G. David, "Advances in bone biology: the osteoclast," Endocr Rev. 17(4):308-332, 1996.
Simonet et al., "Osteoprotegerin: A novel secreted protein involved in the regulation of bone density," Cell 89:309-319, 1997.
Smith, C. et al., "A receptor for tumor necrosis factor defines an unusual family of cellular and viral proteins," Sci. 248:1019-1022, 1990.
Suda et al., "Modulation of osteoclast differentiation by local factors," Bone 17(2):87S-91S; 1995.
Suda et al., "Modulation of osteoclast differentiation," Endocr Rev. 13:66-80, 1992.
Suda et al., "Modulation of osteoclast differentiation: update 1995," in Endocr Rev. Monographs,4(1):266-270; 1995.
Takada et al., "A simple method to assess osteoclast-mediated bone resorption using unfractionated bone cells," Bone Miner., 17:347-359 (1992).
Takahashi N et al., "A new member of tumor necrosis factor ligand family, ODF/OPGL/TRANCE/RANKL, regulates osteoclast differentiation and function," Biochem Biophys Res Commun 1999; 256:449-455.
Tsuda et al., "Isolation of a novel cytokine from human fibroblasts that specifically inhibits osteoclastogenesis," Biochem. Biophys. Res. Commun., 234(1):137-142 (1997).
Tsukii K et al., "Osteoclast differentiation factor mediates an essential signal for bone resorption induced by 1α,25-dihydroxyvitamin D3, prostaglandin E2, or parathyroid hormone in the microenvironment of bone," Biochem Biophys Res Commun 1998; 246:337-341.
Wiley, SR et al., "Identification and characterization of a new member of the TNF family that induces apoptosis," Immunity 1995; 3(6):673-682.
Williams (Ed.), Current Problems in Cancer 1997; pp. 133-169.
Wong et al., "The TRAF family of signal transducers mediates NF-κB activation by the TRANCE receptor," J. Biol. Chem. 273(43):28355-28359, 1998.
Wong et al., "TRANCE (Tumor necrosis factor [TNF]-related activation-induced cytokine), a new TNF family member predominantly expressed in T cells, is a dendritic cell-specific survival factor," J. Exp. Med. 186(12):2075-2080, 1997.
Wong et al., "TRANCE is a novel ligand of the tumor necrosis factor receptor family that activates c-Jun N-terminal kinase in T cells," J. of Biological Chemistry 272(40):25190-25194, 1997.
Xing et al., "Mechanisms by which NF-κB regulates osteoclast numbers," Abstract ASBMR Meeting, U of TX Health Science Center, 1998.
Yasuda et al., "Osteoclast differentiation factor is a ligand for osteoprotegerin/osteoclastogenesis-inhibitory factor and is identical to TRANCE/RANKL," Proc. Natl. Acad. Sci. 95:3597-3602, 1998.
Yun et al., "OPG/FDCR-1, a TNF receptor family member, is expressed in lymphoid cells and is up-regulated by ligating CD401," J. Immunol. 161:6113-6121, 1998.
Read, "Experimental therapies for sepsis directed against tumour necrosis factor," J Antimicrob Chemother 41(Suppl. A):65-69, 1998.

METHOD OF INHIBITING OSTEOCLAST ACTIVITY

CROSS-REFERENCE TO RELATED PATENT APPLICATIONS

This application is a continuation of U.S. patent application Ser. No. 09/705,985 filed Nov. 3, 2000, which is incorporated herein in its entirety, which is a continuation of International patent application No. PCT/US99/10588 filed May 13, 1999, which claims the benefit of U.S. provisional patent applications 60/110,836 filed Dec. 3, 1998 and 60/085,487 filed May 14, 1998, and is a continuation-in-part of U.S. patent application Ser. No. 11/881,911 filed Jul. 30, 2007, which is a divisional of U.S. patent application Ser. No. 10/405,878 filed Apr. 1, 2003 (now U.S. Pat. No. 7,262,274), which is a continuation of U.S. patent application Ser. No. 09/871,291 filed May 30, 2001 (now U.S. Pat. No. 6,562,948), which is a divisional of U.S. patent application Ser. No. 09/577,800 filed May 24, 2000 (now U.S. Pat. No. 6,479,635), which is a continuation of U.S. patent application Ser. No. 09/466,496 filed Dec. 17, 1999 (now U.S. Pat. No. 6,528,482), which is a continuation of U.S. patent application Ser. No. 08/996,139 filed Dec. 22, 1997 (now U.S. Pat. No. 6,017,729), which claims the benefit of U.S. provisional application No. 60/064,671 filed Oct. 14, 1997, U.S. provisional application No. 60/077,181 filed Mar. 7, 1997, and U.S. provisional application No. 60/059,978, filed Dec. 23, 1996.

TECHNICAL FIELD OF THE INVENTION

The present invention relates generally to the field of cytokine receptors, and more specifically to cytokine receptor/ligand pairs having osteoclast regulatory activity.

BACKGROUND OF THE INVENTION

RANK (Receptor Activator of NF-κB) and its ligand (RANKL) are a recently-described receptor/ligand pair that play an important role in an immune response. The cloning of RANK and RANKL is described in U.S. Ser. No. 08/996,139 and U.S. Ser. No. 08/995,659, respectively. It has recently been found that RANKL binds to a protein referred to as osteoprotegerin (OPG), a member of the Tumor Necrosis Factor Receptor (TNFR) family. Yasuda et al. (*Proc. Natl. Acad. Sci.* 95:3597; 1998) expression cloned a ligand for OPG, which they referred to as osteoclastogenesis inhibitory factor. Their work was repeated by Lacey et al. (*Cell* 93:165; 1998). In both cases, the ligand they cloned turned out to be identical to RANKL.

In osteoclastogenesis, the interaction of an osteoblast or stromal cell with an osteoclast precursor leads to the differentiation of the precursor into an osteoclast. OPG was known to inhibit this differentiation. A model has been proposed in which RANKL on the osteoblast or stromal cell surface interacts with a specific receptor on an osteoclast progenitor surface, signaling a differentiation event. OPG effectively blocks the interaction of RANKL with a receptor on osteoclast progenitors in vitro, and has been shown to ameliorate the effects of ovariectomy on bone-loss in mice. However, OPG is also known to bind other ligands in the TNF family, which may have a deleterious effect on the activities of such ligands in vivo. Moreover, the presence of other ligands that bind OPG in vivo may require high dosages of OPG to be administered in order to have sufficient soluble OPG available to inhibit osteoclastogenesis.

Accordingly, there is a need in the art to identify soluble factors that specifically bind RANKL and inhibit the ability of RANKL to induce osteoclastogenesis without reacting with other ligands.

SUMMARY OF THE INVENTION

The present invention provides processes associated with the use of a novel receptor, referred to as RANK (for receptor activator of NF-κB), that is a member of the TNF receptor superfamily. RANK is a Type I transmembrane protein having 616 amino acid residues, comprising an extracellular domain, transmembrane region and cytoplasmic domain. RANK interacts with various TNF Receptor Associated Factors (TRAFs); triggering of RANK results in the upregulation of the transcription factor NF-κB, a ubiquitous transcription factor that is most extensively utilized in cells of the immune system.

Soluble forms of the receptor can be prepared and used to interfere with signal transduction through membrane-bound RANK. Inhibition of RANKL-mediated signal transduction will be useful in ameliorating the effects of osteoclastogenesis and osteoclast activity in disease conditions in which there is excess bone break down. Examples of such conditions include osteoporosis, Paget's disease, cancers that may metastasize to bone and induce bone breakdown (i.e., multiple myeloma, breast cancer, some melanomas; see also Mundy, C. *Cancer Suppl.* 80:1546; 1997), and cancers that do not necessarily metastasize to bone, but result in hypercalcemia and bone loss (e.g. squamous cell carcinomas).

Soluble forms of RANK comprise the extracellular domain of RANK or a fragment thereof that binds RANKL. Fusion proteins of RANK may be made to allow preparation of soluble RANK. Examples of such fusion proteins include a RANK/Fc fusion protein, a fusion protein of a zipper moiety (i.e., a leucine zipper), and various tags that are known in the art. Other antagonists of the interaction of RANK and RANKL (i.e., antibodies to RANKL, small molecules) will also be useful in the inventive methods. These and other aspects of the present invention will become evident upon reference to the following detailed description of the invention.

DETAILED DESCRIPTION OF THE INVENTION

A novel partial cDNA insert with a predicted open reading frame having some similarity to CD40 was identified and was used to hybridize to colony blots generated from a dendritic cell (DC) cDNA library containing full-length cDNAs. SEQ ID NO:1 shows the nucleotide and amino acid sequence of a predicted full-length protein.

RANK is a member of the TNF receptor superfamily; it most closely resembles CD40 in the extracellular region. RANK is expressed on epithelial cells, some B cell lines, and on activated T cells. However, its expression on activated T cells is late, about four days after activation. This time course of expression coincides with the expression of Fas, a known agent of apoptosis. RANK may act as an anti-apoptotic signal, rescuing cells that express RANK from apoptosis as CD40 is known to do. Alternatively, RANK may confirm an apoptotic signal under the appropriate circumstances, again similar to CD40. RANK and its ligand are likely to play an integral role in regulation of the immune and inflammatory response. The isolation of a DNA encoding RANK is described in U.S. Ser. No. 08/996,139, filed Dec. 22, 1997, the disclosure of which is incorporated by reference herein.

U.S. Ser. No. 08/996,139 describes several forms of RANK that are useful in the present invention.

Soluble RANK comprises the signal peptide and the extracellular domain (residues 1 to 213 of SEQ ID NO:2) or a fragment thereof. Alternatively, a different signal peptide can be substituted for the native leader, beginning with residue 1 and continuing through a residue selected from the group consisting of amino acids 24 through 33 (inclusive) of SEQ ID NO:2. Other members of the TNF receptor superfamily have a region of amino acids between the transmembrane domain and the ligand binding domain that is referred to as a 'spacer' region, which is not necessary for ligand binding. In RANK, the amino acids between 196 and 213 are predicted to form such a spacer region. Accordingly, a soluble form of RANK that terminates with an amino acid in this region is expected to retain the ability to bind a ligand for RANK in a specific manner. Preferred C-terminal amino acids for soluble RANK peptides are selected from the group consisting of amino acids 213 and 196 of SEQ ID NO:2, although other amino acids in the spacer region may be utilized as a C-terminus. In muRANK, the amino acids between 197 and 214 are predicted to form such a spacer region. Accordingly, a soluble form of RANK that terminates with an amino acid in this region is expected to retain the ability to bind a ligand for RANK in a specific manner. Preferred C-terminal amino acids for soluble RANK peptides are selected from the group consisting of amino acids 214, and 197 of SEQ ID NO:5, although other amino acids in the spacer region may be utilized as a C-terminus. Moreover, fragments of the extracellular domain will also provide soluble forms of RANK.

Fragments can be prepared using known techniques to isolate a desired portion of the extracellular region, and can be prepared, for example, by comparing the extracellular region with those of other members of the TNFR family (of which RANK is a member) and selecting forms similar to those prepared for other family members. Alternatively, unique restriction sites or PCR techniques that are known in the art can be used to prepare numerous truncated forms which can be expressed and analyzed for activity.

Other derivatives of the RANK proteins within the scope of this invention include covalent or aggregative conjugates of the proteins or their fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Protein fusions can comprise peptides added to facilitate purification or identification of RANK proteins and homologs (e.g., poly-His). The amino acid sequence of the inventive proteins can also be linked to an identification peptide such as that described by Hopp et al., *Bio/Technology* 6:1204 (1988; FLAG™). Such a highly antigenic peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein.

Fusion proteins further comprise the amino acid sequence of a RANK linked to an immunoglobulin Fc region. An exemplary Fc region is a human $IgG_1$ having an amino acid sequence set forth in SEQ ID NO:3. Fragments of an Fc region may also be used, as can Fc muteins. For example, certain residues within the hinge region of an Fc region are critical for high affinity binding to FcγRI. Canfield and Morrison (*J. Exp. Med.* 173:1483; 1991) reported that $Leu_{(234)}$ and $Leu_{(235)}$ were critical to high affinity binding of $IgG_3$ to FcγRI present on U937 cells. Similar results were obtained by Lund et al. (*J. Immunol.* 147:2657, 1991; *Molecular Immunol.* 29:53, 1991). Such mutations, alone or in combination, can be made in an $IgG_1$ Fc region to decrease the affinity of $IgG_1$ for FcR. Depending on the portion of the Fc region used, a fusion protein may be expressed as a dimer, through formation of interchain disulfide bonds. If the fusion proteins are made with both heavy and light chains of an antibody, it is possible to form a protein oligomer with as many as four RANK regions.

In another embodiment, RANK proteins further comprise an oligomerizing peptide such as a zipper domain. Leucine zippers were originally identified in several DNA-binding proteins (Landschulz et al., *Science* 240:1759, 1988). Zipper domain is a term used to refer to a conserved peptide domain present in these (and other) proteins, which is responsible for multimerization of the proteins. The zipper domain comprises a repetitive heptad repeat, with four or five leucine, isoleucine or valine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240:1759, 1988). The products of the nuclear oncogenes fos and jun comprise zipper domains that preferentially form a heterodimer (O'Shea et al., *Science* 245:646, 1989; Turner and Tjian, *Science* 243:1689, 1989). A preferred zipper moiety is that of SEQ ID NO:6 or a fragment thereof. This and other zippers are disclosed in U.S. Pat. No. 5,716,805.

Other embodiments of useful proteins include RANK polypeptides encoded by DNAs capable of hybridizing to the DNA of SEQ ID NO:1 under moderately stringent conditions (prewashing solution of 5×SSC, 0.5% SDS, 1.0 mM EDTA (pH 8.0) and hybridization conditions of 50° C., 5×SSC, overnight) to the DNA sequences encoding RANK, or more preferably under stringent conditions (for example, hybridization in 6×SSC at 63° C. overnight; washing in 3×SSC at 55° C.), and other sequences which are degenerate to those which encode the RANK. In one embodiment, RANK polypeptides are at least about 70% identical in amino acid sequence to the amino acid sequence of native RANK protein as set forth in SEQ ID NO:2 for human RANK and NO:5 for murine RANK. In a preferred embodiment, RANK polypeptides are at least about 80% identical in amino acid sequence to the native form of RANK; most preferred polypeptides are those that are at least about 90% identical to native RANK.

Percent identity may be determined using a computer program, for example, the GAP computer program described by Devereux et al. (*Nucl. Acids Res.* 12:387, 1984) and available from the University of Wisconsin Genetics Computer Group (UWGCG). For fragments derived from the RANK protein, the identity is calculated based on that portion of the RANK protein that is present in the fragment.

The biological activity of RANK analogs or muteins can be determined by testing the ability of the analogs or muteins to bind RANKL (SEQ ID NOS:7 and 8, for example as described in the Examples herein. Suitable assays include, for example, an enzyme immunoassay or a dot blot, and assays that employ cells expressing RANKL. Suitable assays also include, for example, inhibition assays, wherein soluble RANK is used to inhibit the interaction of RANKL with membrane-bound or solid-phase associated RANK (i.e., signal transduction assays). Such methods are well known in the art.

RANKL and RANK are important factors in osteoclastogenesis. RANK is expressed on osteoclasts and interacts with RANK ligand (RANKL) to mediate the formation of osteoclast-like (OCL) multinucleated cells. This was shown by treating mouse bone marrow preparations with M-CSF (CSF-1) and soluble RANKL for 7 days in culture. No additional osteoclastogenic hormones or factors were necessary for the generation of the multinucleated cells. Neither M-CSF nor RANKL alone led to the formation of OCL. The multinucleated cells expressed tartrate resistant acid phosphatase and were positive for [125] calcitonin binding. The tyrosine kinase c-src was highly expressed in multinucleated OCL and a subset of mononuclear cells as demonstrated by immunofluorescence microscopy. (See Example 2).

Purification of Recombinant RANK

Purified RANK, and homologs or analogs thereof are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit.

Following the concentration step, the concentrate can be applied to a suitable purification matrix. For example, a suitable affinity matrix can comprise a counter structure protein or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying the inventive proteins.

Affinity chromatography is a particularly preferred method of purifying RANK and homologs thereof. For example, a RANK expressed as a fusion protein comprising an immunoglobulin Fc region can be purified using Protein A or Protein G affinity chromatography. Moreover, a RANK protein comprising an oligomerizing zipper domain may be purified on a resin comprising an antibody specific to the oligomerizing zipper domain. Monoclonal antibodies against the RANK protein may also be useful in affinity chromatography purification, by utilizing methods that are well-known in the art. A ligand may also be used to prepare an affinity matrix for affinity purification of RANK.

Finally, one or more reversed-phase high performance liquid chromatography (RP-HPLC) steps employing hydrophobic RP-HPLC media, e.g., silica gel having pendant methyl or other aliphatic groups, can be employed to further purify a RANK composition. Suitable methods include those analogous to the method disclosed by Urdal et al. (*J. Chromatog.* 296:171, 1984). Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant protein can be disrupted by any convenient method, including freeze-thaw cycling, sonication, mechanical disruption, or use of cell lysing agents. Fermentation of yeast which express the inventive protein as a secreted protein greatly simplifies purification.

Protein synthesized in recombinant culture is characterized by the presence of cell components, including proteins, in amounts and of a character which depend upon the purification steps taken to recover the inventive protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of the inventive proteins free of other proteins which may be normally associated with the proteins as they are found in nature in the species of origin.

Uses and Administration of RANK Compositions

The present invention provides methods of using therapeutic compositions comprising a protein and a suitable diluent and carrier. These methods involve the use of therapeutic compositions of RANK or soluble fragments of RANK for regulating an immune or inflammatory response. Further included within the present invention are methods for regulating osteoclast activity by administering therapeutic compositions of RANK or soluble RANK fragments to an individual in amounts sufficient to decrease excess bone resorption. Typically, the individual is inflicted with excess bone resorption and suffers from the effects of hypercalcemia, has symptoms of hypercalcemia, or is suffering a disease that involves excessive bone resorption. In addition to regulating osteoclast activity, the methods described herein are applicable to inhibiting osteoclast activity, regulating osteoclast generation and inhibiting osteoclast generation in individuals inflicted with excess bone resorption. In connection with the methods described herein, the present invention contemplates the use of RANK in conjunction with soluble cytokine receptors or cytokines, or other osteoclast/osteoblast regulatory molecules.

Soluble forms of RANK and other RANK antagonists such as antagonistic monoclonal antibodies can be administered for the purpose of inhibiting RANK-induced induction of NF-κB activity. NF-κB is a transcription factor that is utilized extensively by cells of the immune system, and plays a role in the inflammatory response. Thus, inhibitors of RANK signalling will be useful in treating conditions in which signalling through RANK has given rise to negative consequences, for example, toxic or septic shock, or graft-versus-host reactions. They may also be useful in interfering with the role of NF-κB in cellular transformation. Tumor cells are more responsive to radiation when their NF-κB is blocked; thus, soluble RANK (or other antagonists of RANK signalling) will be useful as an adjunct therapy for disease characterized by neoplastic cells that express RANK.

In connection with the methods described herein, RANK ligand (RANKL) on osteoblasts or stromal cells is known to interact with RANK on osteoclast progenitor surfaces signaling an event that leads to the differentiation of osteoclast precursors into osteoclasts. (See Example 2 below.) Thus, RANK, and in particular soluble forms of RANK, is useful for the inhibition of the RANKL-mediated signal transduction that leads to the differentiation of osteoclast precursors into osteoclasts. Soluble forms of RANK are also useful for the regulation and inhibition of osteoclast activity, e.g. bone resorption. By interfering with osteoclast differentiation, soluble forms of RANK are useful in the amelioration of the effects of osteoclastogenesis in disease conditions in which there is excess bone break down. Such disease conditions include Paget's disease, osteoporosis, and cancer. Many cancers metastasize to bone and induce bone breakdown by locally disrupting normal bone remodeling. Such cancers can be associated with enhanced numbers of osteoclasts and enhanced amount of osteoclastic bone resorption resulting in hypercalcemia. These cancers include, but are not limited to, breast cancer, multiple myeloma, melanomas, lung cancer, prostrate, hematologic, head and neck, and renal. (See Guise et al. *Endocrine Reviews*, 19(1):18-54, 1998.) Soluble forms of RANK can be administered to such cancer patients to disrupt the osteoclast differentiation pathway and result in fewer numbers of osteoclast, less bone resorption, and relief from the negative effects of hypercalcemia.

Other cancers do not metastasize to bone, but are known to act systemically on bone to disrupt bone remodeling and result in hypercalcemia. (See Guise et al. Endocrine Reviews, 19(1):18-54, 1998.) In accordance with this invention, RANKL has been found on the surface of certain squamous cells that do not metastasize to bone but are associated with hypercalcemia. (See Example 3 below) Squamous cells that are associated with hypercalcemia also express M-CSF (CSF-1), a cytokine that, together with RANKL, stimulates the proliferation and differentiation of osteoclast precursors to osteoclasts. In accordance with the present invention, it has been discovered that M-CSF directly upregulates RANK on surfaces of osteoclast precursors. When squamous cells release excessive amounts of CSF-1, increased expression of RANK occurs on the surfaces of osteoclast precursors. Thus, there is a higher probability that RANK will interact with RANKL on osteoblasts or stromal cells to produce increased numbers of osteoclasts, resulting in an enhanced amount of bone break down and hypercalcemia.

In addition to the ameliorating the effects of cancers that metastasize to bone, the present invention provides methods for ameliorating the systemic effects, e.g. hypercalcemia, of cancers that are associated with excess osteoclast activity (e.g. squamous cell carcinomas). Such methods include administering soluble forms of RANK in amounts sufficient to interfere with the RANK/RANKL signal transduction that leads to the differentiation of osteoclast precursors into osteoclasts. Fewer osteoclasts lead to reduced bone resorption and relief from the negative effects of hypercalcemia.

For therapeutic use, purified protein is administered to an individual, preferably a human, for treatment in a manner appropriate to the indication. Thus, for example, RANK protein compositions administered to regulate osteoclast function can be given by bolus injection, continuous infusion, sustained release from implants, or other suitable technique. Typically, a therapeutic agent will be administered in the form of a composition comprising purified RANK, in conjunction with physiologically acceptable carriers, excipients or diluents. Such carriers will be nontoxic to recipients at the dosages and concentrations employed.

Ordinarily, the preparation of such protein compositions entails combining the inventive protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with con-specific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

Soluble forms of RANK and other RANK antagonists such as antagonistic monoclonal antibodies can be administered for the purpose of inhibiting RANK-induced osteoclastogenesis. It is desirable to inhibit osteoclastogenesis in various disease states in which excess bone loss occurs. Examples include osteoporosis, Pagett's disease, and various cancers. Various animal models of these diseases are known in the art; accordingly, it is a matter of routine experimentation to determine optimal dosages and routes of administration of soluble RANK, first in an animal model and then in human clinical trials.

The following examples are offered by way of illustration, and not by way of limitation. Those skilled in the art will recognize that variations of the invention embodied in the examples can be made, especially in light of the teachings of the various references cited herein, the disclosures of which are incorporated by reference.

EXAMPLE 1

This example describes a plate binding assay useful in comparing the ability of various ligands to bind receptors. The assay is performed essentially as described in Smith et al., Virology 236:316 (1997). Briefly, 96-well microtiter plates are coated with an antibody to human Fc (i.e., polyclonal goat anti human Fc). Receptor/Fc fusion proteins are then added, and after incubation, the plates are washed. Serial dilutions of the ligands are then added. The ligands may be directly labeled (i.e., with 1251), or a detecting reagent that is radioactively labeled may be used. After incubation, the plates are washed, specifically bound ligands are released, and the amount of ligand bound quantified.

Using this method, RANK/Fc and OPG/Fc were bound to 96-well plates. In an indirect method, a RANKL/zipper fusion is detected using a labeled antibody to the zipper moiety. It was found that human OPG/Fc binds mRANKL at 0.05 nM, and human RANK/Fc binds mRANKL at 0.1 nM. These values indicate similar binding affinities of OPG and RANK for RANKL, confirming the utility of RANK as an inhibitor of osteoclast activity in a manner similar to OPG.

EXAMPLE 2

The following describes the formation of osteoclast like cells from bone marrow cell cultures using a soluble RANKL in the form of soluble RANKL/leucine zipper fusion protein (RANKL LZ).

Using RANKL LZ at 1 µg/ml, osteoclasts were generated from murine bone marrow (BM) in the presence of CSF-1. These osteoclasts are formed by the fusion of macrophage-like cells and are characterized by their TRAP (tartrate-resistant acid phosphatase) positivity. No TRAP$^+$ cells were seen in cultures containing CSF-1 alone or in cultures containing CSF-1 and TRAIL LZ (a control for the soluble RANKL LZ). Even though human and monkey bone marrow contains more contaminating fibroblasts than murine bone marrow, osteoclasts were generated from murine and monkey bone marrow with the combination of CSF-1 and soluble RANKL LZ. In a dose-response study using murine bone marrow and suboptimal amounts of CSF-1 (40 ng/ml), the effects of soluble RANKL LZ plateaued at about 100 ng/ml.

The effect of soluble RANKL LZ on proliferation of cells was studied in the same cultures using Alamar Blue. After 5 days, the proliferative response was lower in cultures containing CSF-1 and RANKL LZ than in those containing CSF-1 alone. The supports the observation that soluble RANKL LZ is inducing osteoclast differentiation. When CSF-1 and RANKL LZ are washed out of murine BM cultures at day 7 or 8, cells do not survive if they are recultured in medium or in RANKL LZ alone. In contrast, cells do survive if recultured in CSF-1. When RANKL LZ was added to these cultures there was no added benefit. Thus, the combination of CSF-1 and RANKL are required for the generation of osteoclast. Additionally, once formed, CSF-1 is sufficient to maintain their survival in culture.

Finally, using human bone marrow, soluble anti-human RANK mAb and immobilized anti-human RANK mAb were compared to RANKL LZ for the generation of osteoclasts in the presence of CSF-1. Immobilized M331 and RANKL LZ were found to be equally effective for osteoclast generation while soluble M331 was superior to both immobilized antibody and RANKL LZ. This confirms that the osteoclast differentiating activity of RANKL is mediated through RANK rather than via an alternative receptor.

Since osteoclasts cannot readily be harvested and analyzed by flow cytometry, $^{125}$I-labeled calcitonin binding assays were used to identify osteoclasts (the calcitonin receptor is considered to be an osteoclast-specific marker). Osteoclasts generated from murine BM cultured with CSF-1 and RANKL LZ for 9 days showed binding of radiolabeled calcitonin confirming their osteoclast identity.

EXAMPLE 3

In order to determine RANKL expression by either of two different squamous cell carcinomas, standard Western blot and RT-PCR studies were performed on MH-85 and OKK cells. One of these carcinoma cells, the MH-85 cells, is associated with hypercalcemia.

The results confirmed that MH-85 and OKK squamous cells express RANKL. MH-85 cells, in addition to being linked with hypercalcemia in patients inflicted with this carcinoma, also express M-CSF (CSF-1). It was also determined that CSF-1 upregulates RANK expression on osteoclast precursors. The enhanced amount of CSF-1 in MH-85 type squamous cell cancer patients can lead to an upregulation of RANK and increased RANK interaction with RANKL. Signals transduced by RANK and RANKL interaction result in increased numbers of mature osteoclasts and bone breakdown. Since soluble forms of RANK can inhibit the RANK/RANKL interaction, administering a soluble form of RANK (e.g. the extracellular region of RANK fused to an Fc) to a squamous cell cancer patient provides relief from adverse effects of this cancer, including hypercalcemia.

We claim:

1. A method of inhibiting RANKL-induced osteoclastogenesis in a patient in need thereof, comprising administering to said patient a soluble RANK polypeptide composition comprising a soluble RANK polypeptide, wherein
said patient suffers from a condition selected from the group consisting of bone cancer, multiple myeloma, melanoma and breast cancer,
the soluble RANK polypeptide comprises amino acids 33-196 of SEQ ID NO:2 and is capable of binding to a RANKL polypeptide that consists of amino acids 1-317 of SEQ ID NO:8, and
said composition is administered in an amount sufficient to inhibit RANKL-induced osteoclastogenesis in said patient.

2. The method of claim 1, wherein the soluble RANK polypeptide further comprises a polypeptide selected from the group consisting of an immunoglobulin Fc domain, an immunoglobulin Fc mutein, a FLAG™ tag, a peptide comprising at least 6 His residues, a leucine zipper, and combinations thereof.

3. The method of claim 1, wherein the soluble RANK polypeptide comprises amino acids 33-213 of SEQ ID NO:2.

4. A method of inhibiting RANKL-induced osteoclastogenesis in a patient in need thereof, said method comprising administering to said patient a composition comprising a recombinant soluble RANK polypeptide, wherein
said patient suffers from a condition selected from the group consisting of squamous cell carcinoma, lung cancer, prostate cancer, hematologic cancer, head and neck cancer and renal cancer,
the soluble RANK polypeptide comprises amino acids 33-196 of SEQ ID NO:2 and is capable of binding to a RANKL polypeptide that consists of amino acids 1-317 of SEQ ID NO:8, and
said composition is administered in an amount sufficient to inhibit RANKL-induced osteoclastogenesis in said patient.

5. The method of claim 4, wherein the soluble RANK polypeptide comprises amino acids 33-213 of SEQ ID NO:2.

6. The method of claim 4, wherein the soluble RANK polypeptide further comprises one or more polypeptides selected from the group consisting of an immunoglobulin Fc domain, an immunoglobulin Fc mutein, a FLAG™ tag, a peptide comprising at least 6 His residues and a leucine zipper.

7. A method according to claim 2, wherein the further polypeptide is selected from the group consisting of an immunoglobulin Fc domain comprising the amino acid sequence as shown in SEQ ID NO:3 and a leucine zipper comprising the amino acid sequence as shown in SEQ ID NO:6.

8. A method according to claim 6, wherein the further polypeptide is selected from the group consisting of an immunoglobulin Fc domain having the amino acid sequence as shown in SEQ ID NO:3 and a leucine zipper having the amino acid sequence as shown in SEQ ID NO:6.

9. A method according to claim 7, wherein the soluble RANK polypeptide consists of amino acids 33-213 of SEQ ID NO:2 fused with the amino acid sequence as shown in SEQ ID NO:3.

10. A method according to claim 8, wherein the soluble RANK polypeptide consists of amino acids 33-213 of SEQ ID NO:2 fused with the amino acid sequence as shown in SEQ ID NO:3.

* * * * *

UNITED STATES PATENT AND TRADEMARK OFFICE
CERTIFICATE OF CORRECTION

PATENT NO. : 7,790,684 B2
APPLICATION NO. : 12/137397
DATED : September 7, 2010
INVENTOR(S) : Dirk M. Anderson and Laurent J. Galibert Page 1 of 2

It is certified that error appears in the above-identified patent and that said Letters Patent is hereby corrected as shown below:

Title Page,
Item (60) (first occurrence): "Continuation of application No. 09/705,985, filed on Nov. 3, 2000, now abandoned, which is a continuation of application No. PCT/US99/10588, filed on May 13, 1999, application No. 12/137,397, which is a continuation-in-part of application No. 11/881,911, filed on Jul. 30, 2007, which is a continuation-in-part of application No. 10/405,878, filed on Apr. 1, 2003, now Pat. No. 7,262,274, which is a continuation of application No. 09/871,291, filed on May 30, 2001, now Pat. No. 6,562,948, which is a division of application No. 09/577,800, filed on May 24, 2000, now Pat. No. 6,479,635, which is a continuation of application No. 09/466,496, filed on Dec. 17, 1999, now Pat. No. 6,528,482, which is a continuation of application Ser. No. 08/996,139, filed on Dec. 22, 1997, now Pat. No. 6,017,729."

Should read:

-- Continuation of application No. 09/705,985, filed on Nov. 3, 2000, now abandoned, which is a continuation of application No. PCT/US99/10588, filed on May 13, 1999, and application No. 12/137,397 is a continuation-in-part of application No. 11/881,911, filed on Jul. 30, 2007, which is a divisional of application No. 10/405,878, filed on Apr. 1, 2003, now Pat. No. 7,262,274, which is a continuation of application No. 09/871,291, filed on May 30, 2001, now Pat. No. 6,562,948, which is a division of application No. 09/577,800, filed on May 24, 2000, now Pat. No. 6,479,635, which is a continuation of application No. 09/466,496, filed on Dec. 17, 1999, now Pat. No. 6,528,482, which is a continuation of application Ser. No. 08/996,139, filed on Dec. 22, 1997, now Pat. No. 6,017,729. --

Signed and Sealed this
Eighteenth Day of February, 2014

Michelle K. Lee
*Deputy Director of the United States Patent and Trademark Office*

CERTIFICATE OF CORRECTION (continued)
U.S. Pat. No. 7,790,684 B2

In the Specification

Col. 8, line 34: "(i.e., with 125l)," should read -- (i.e., with $^{125}$I), --

SEQUENCE LISTING

<160> NUMBER OF SEQ ID NOS: 8

<210> SEQ ID NO 1
<211> LENGTH: 3136
<212> TYPE: DNA
<213> ORGANISM: Homo sapiens
<220> FEATURE:
<221> NAME/KEY: CDS
<222> LOCATION: (39)..(1886)
<223> OTHER INFORMATION:

<400> SEQUENCE: 1

```
ccgctgaggc cgcggcgccc gccagcctgt cccgcgcc atg gcc ccg cgc gcc cgg      56
                                          Met Ala Pro Arg Ala Arg
                                            1               5 cgg cgc cgc ccg ctg ttc gcg ctg ctg ctc tgc gcg ctc ctc gcc          104
Arg Arg Arg Pro Leu Phe Ala Leu Leu Leu Cys Ala Leu Leu Ala
             10                  15                  20 cgg ctg cag gtg gct ttg cag atc gct cct cca tgt acc agt gag aag      152
Arg Leu Gln Val Ala Leu Gln Ile Ala Pro Pro Cys Thr Ser Glu Lys
         25                  30                  35 cat tat gag cat ctg gga cgg tgc tgt aac aaa tgt gaa cca gga aag      200
His Tyr Glu His Leu Gly Arg Cys Cys Asn Lys Cys Glu Pro Gly Lys
     40                  45                  50 tac atg tct tct aaa tgc act act acc tct gac agt gta tgt ctg ccc      248
Tyr Met Ser Ser Lys Cys Thr Thr Thr Ser Asp Ser Val Cys Leu Pro
 55                  60                  65                  70 tgt ggc ccg gat gaa tac ttg gat agc tgg aat gaa gaa gat aaa tgc      296
Cys Gly Pro Asp Glu Tyr Leu Asp Ser Trp Asn Glu Glu Asp Lys Cys
                 75                  80                  85 ttg ctg cat aaa gtt tgt gat aca ggc aag gcc ctg gtg gcc gtg gtc      344
Leu Leu His Lys Val Cys Asp Thr Gly Lys Ala Leu Val Ala Val Val
             90                  95                 100 gcc ggc aac agc acg acc ccc cgg cgc tgc gcg tgc acg gct ggg tac      392
```

-continued

| | | |
|---|---|---|
| Ala Gly Asn Ser Thr Thr Pro Arg Arg Cys Ala Cys Thr Ala Gly Tyr<br>        105                           110                   115 | | |
| cac tgg agc cag gac tgc gag tgc tgc cgc cgc aac acc gag tgc gcg<br>His Trp Ser Gln Asp Cys Glu Cys Cys Arg Arg Asn Thr Glu Cys Ala<br>120                       125                       130 | | 440 |
| ccg ggc ctg ggc gcc cag cac ccg ttg cag ctc aac aag gac aca gtg<br>Pro Gly Leu Gly Ala Gln His Pro Leu Gln Leu Asn Lys Asp Thr Val<br>135                     140                     145                     150 | | 488 |
| tgc aaa cct tgc ctt gca ggc tac ttc tct gat gcc ttt tcc tcc acg<br>Cys Lys Pro Cys Leu Ala Gly Tyr Phe Ser Asp Ala Phe Ser Ser Thr<br>                     155                     160                     165 | | 536 |
| gac aaa tgc aga ccc tgg acc aac tgt acc ttc ctt gga aag aga gta<br>Asp Lys Cys Arg Pro Trp Thr Asn Cys Thr Phe Leu Gly Lys Arg Val<br>                 170                     175                     180 | | 584 |
| gaa cat cat ggg aca gag aaa tcc gat gcg gtt tgc agt tct tct ctg<br>Glu His His Gly Thr Glu Lys Ser Asp Ala Val Cys Ser Ser Ser Leu<br>               185                     190                     195 | | 632 |
| cca gct aga aaa cca cca aat gaa ccc cat gtt tac ttg ccc ggt tta<br>Pro Ala Arg Lys Pro Pro Asn Glu Pro His Val Tyr Leu Pro Gly Leu<br>200                       205                       210 | | 680 |
| ata att ctg ctt ctc ttc gcg tct gtg gcc ctg gtg gct gcc atc atc<br>Ile Ile Leu Leu Leu Phe Ala Ser Val Ala Leu Val Ala Ala Ile Ile<br>215                     220                     225                     230 | | 728 |
| ttt ggc gtt tgc tat agg aaa aaa ggg aaa gca ctc aca gct aat ttg<br>Phe Gly Val Cys Tyr Arg Lys Lys Gly Lys Ala Leu Thr Ala Asn Leu<br>                     235                     240                     245 | | 776 |
| tgg cac tgg atc aat gag gct tgt ggc cgc cta agt gga gat aag gag<br>Trp His Trp Ile Asn Glu Ala Cys Gly Arg Leu Ser Gly Asp Lys Glu<br>               250                     255                     260 | | 824 |
| tcc tca ggt gac agt tgt gtc agt aca cac acg gca aac ttt ggt cag<br>Ser Ser Gly Asp Ser Cys Val Ser Thr His Thr Ala Asn Phe Gly Gln<br>             265                     270                     275 | | 872 |
| cag gga gca tgt gaa ggt gtc tta ctg ctg act ctg gag gag aag aca<br>Gln Gly Ala Cys Glu Gly Val Leu Leu Leu Thr Leu Glu Glu Lys Thr<br>        280                     285                     290 | | 920 |
| ttt cca gaa gat atg tgc tac cca gat caa ggt ggt gtc tgt cag ggc<br>Phe Pro Glu Asp Met Cys Tyr Pro Asp Gln Gly Gly Val Cys Gln Gly<br>295                       300                     305                     310 | | 968 |
| acg tgt gta gga ggt ggt ccc tac gca caa ggc gaa gat gcc agg atg<br>Thr Cys Val Gly Gly Gly Pro Tyr Ala Gln Gly Glu Asp Ala Arg Met<br>                     315                     320                     325 | | 1016 |
| ctc tca ttg gtc agc aag acc gag ata gag gaa gac agc ttc aga cag<br>Leu Ser Leu Val Ser Lys Thr Glu Ile Glu Glu Asp Ser Phe Arg Gln<br>                     330                     335                     340 | | 1064 |
| atg ccc aca gaa gat gaa tac atg gac agg ccc tcc cag ccc aca gac<br>Met Pro Thr Glu Asp Glu Tyr Met Asp Arg Pro Ser Gln Pro Thr Asp<br>        345                     350                     355 | | 1112 |
| cag tta ctg ttc ctc act gag cct gga agc aaa tcc aca cct cct ttc<br>Gln Leu Leu Phe Leu Thr Glu Pro Gly Ser Lys Ser Thr Pro Pro Phe<br>360                       365                       370 | | 1160 |
| tct gaa ccc ctg gag gtg ggg gag aat gac agt tta agc cag tgc ttc<br>Ser Glu Pro Leu Glu Val Gly Glu Asn Asp Ser Leu Ser Gln Cys Phe<br>375                       380                     385                     390 | | 1208 |
| acg ggg aca cag agc aca gtg ggt tca gaa agc tgc aac tgc act gag<br>Thr Gly Thr Gln Ser Thr Val Gly Ser Glu Ser Cys Asn Cys Thr Glu<br>                     395                     400                     405 | | 1256 |
| ccc ctg tgc agg act gat tgg act ccc atg tcc tct gaa aac tac ttg<br>Pro Leu Cys Arg Thr Asp Trp Thr Pro Met Ser Ser Glu Asn Tyr Leu<br>                     410                     415                     420 | | 1304 |

```
caa aaa gag gtg gac agt ggc cat tgc ccg cac tgg gca gcc agc ccc      1352
Gln Lys Glu Val Asp Ser Gly His Cys Pro His Trp Ala Ala Ser Pro
        425                 430                 435 agc ccc aac tgg gca gat gtc tgc aca ggc tgc cgg aac cct cct ggg      1400
Ser Pro Asn Trp Ala Asp Val Cys Thr Gly Cys Arg Asn Pro Pro Gly
440                 445                 450 gag gac tgt gaa ccc ctc gtg ggt tcc cca aaa cgt gga ccc ttg ccc      1448
Glu Asp Cys Glu Pro Leu Val Gly Ser Pro Lys Arg Gly Pro Leu Pro
455                 460                 465                 470 cag tgc gcc tat ggc atg ggc ctt ccc cct gaa gaa gaa gcc agc agg      1496
Gln Cys Ala Tyr Gly Met Gly Leu Pro Pro Glu Glu Glu Ala Ser Arg
                475                 480                 485 acg gag gcc aga gac cag ccc gag gat ggg gct gat ggg agg ctc cca      1544
Thr Glu Ala Arg Asp Gln Pro Glu Asp Gly Ala Asp Gly Arg Leu Pro
            490                 495                 500 agc tca gcg agg gca ggt gcc ggg tct gga agc tcc cct ggt ggc cag      1592
Ser Ser Ala Arg Ala Gly Ala Gly Ser Gly Ser Ser Pro Gly Gly Gln
        505                 510                 515 tcc cct gca tct gga aat gtg act gga aac agt aac tcc acg ttc atc      1640
Ser Pro Ala Ser Gly Asn Val Thr Gly Asn Ser Asn Ser Thr Phe Ile
520                 525                 530 tcc agc ggg cag gtg atg aac ttc aag ggc gac atc atc gtg gtc tac      1688
Ser Ser Gly Gln Val Met Asn Phe Lys Gly Asp Ile Ile Val Val Tyr
535                 540                 545                 550 gtc agc cag acc tcg cag gag ggc gcg gcg gcg gct gcg gag ccc atg      1736
Val Ser Gln Thr Ser Gln Glu Gly Ala Ala Ala Ala Ala Glu Pro Met
                555                 560                 565 ggc cgc ccg gtg cag gag gag acc ctg gcg cgc cga gac tcc ttc gcg      1784
Gly Arg Pro Val Gln Glu Glu Thr Leu Ala Arg Arg Asp Ser Phe Ala
            570                 575                 580 ggg aac ggc ccg cgc ttc ccg gac ccg tgc ggc ggc ccc gag ggg ctg      1832
Gly Asn Gly Pro Arg Phe Pro Asp Pro Cys Gly Gly Pro Glu Gly Leu
        585                 590                 595 cgg gag ccg gag aag gcc tcg agg ccg gtg cag gag caa ggc ggg gcc      1880
Arg Glu Pro Glu Lys Ala Ser Arg Pro Val Gln Glu Gln Gly Gly Ala
600                 605                 610 aag gct tgagcgcccc ccatggctgg gagcccgaag ctcggagcca gggctcgcga       1936
Lys Ala
615 gggcagcacc gcagcctctg ccccagcccc ggccacccag ggatcgatcg gtacagtcga    1996 ggaagaccac ccggcattct ctgcccactt tgccttccag gaaatgggct tttcaggaag    2056 tgaattgatg aggactgtcc ccatgccac ggatgctcag cagcccgccg cactggggca     2116 gatgtctccc ctgccactcc tcaaactcgc agcagtaatt tgtggcacta tgacagctat    2176 ttttatgact atcctgttct gtgggggggg ggtctatgtt ttcccccat atttgtattc     2236 cttttcataa cttttcttga tatctttcct ccctcttttt taatgtaaag gttttctcaa    2296 aaattctcct aaaggtgagg gtctctttct tttctctttt ccttttttt ttcttttttt     2356 ggcaacctgg ctctggccca ggctagagtg cagtggtgcg attatagccc ggtgcagcct    2416 ctaactcctg ggctcaagca atccaagtga tcctcccacc tcaaccttcg gagtagctgg    2476 gatcacagct gcaggccacg cccagcttcc tccccgac tccccccccc cagagacacg      2536 gtcccaccat gttacccagc ctggtctcaa actcccagc taaagcagtc ctccagcctc     2596 ggcctcccaa agtactggga ttacaggcgt gagcccccac gctggcctgc tttacgtatt    2656 ttcttttgtg cccctgctca cagtgtttta gagatggctt tcccagtgtg tgttcattgt    2716 aaacactttt gggaaagggc taaacatgtg aggcctggag atagttgcta agttgctagg    2776
```

-continued

```
aacatgtggt gggactttca tattctgaaa aatgttctat attctcattt ttctaaaaga  2836
aagaaaaaag gaaacccgat ttatttctcc tgaatctttt taagtttgtg tcgttcctta  2896
agcagaacta agctcagtat gtgaccttac ccgctaggtg gttaatttat ccatgctggc  2956
agaggcactc aggtacttgg taagcaaatt tctaaaactc caagttgctg cagcttggca  3016
ttcttcttat tctagaggtc tctctggaaa agatggagaa aatgaacagg acatggggct  3076
cctggaaaga aagggcccgg gaagttcaag gaagaataaa gttgaaattt taaaaaaaaa  3136
```

<210> SEQ ID NO 2
<211> LENGTH: 616
<212> TYPE: PRT
<213> ORGANISM: Homo sapiens

<400> SEQUENCE: 2

```
Met Ala Pro Arg Ala Arg Arg Arg Pro Leu Phe Ala Leu Leu Leu
1               5                   10                  15

Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
        35                  40                  45

Lys Cys Glu Pro Gly Lys Tyr Met Ser Ser Lys Cys Thr Thr Thr Ser
    50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95

Ala Leu Val Ala Val Ala Gly Asn Ser Thr Thr Pro Arg Arg Cys
            100                 105                 110

Ala Cys Thr Ala Gly Tyr His Trp Ser Gln Asp Cys Glu Cys Cys Arg
        115                 120                 125

Arg Asn Thr Glu Cys Ala Pro Gly Leu Gly Ala Gln His Pro Leu Gln
    130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
        195                 200                 205

Val Tyr Leu Pro Gly Leu Ile Ile Leu Leu Phe Ala Ser Val Ala
    210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
                245                 250                 255

Leu Ser Gly Asp Lys Glu Ser Ser Gly Asp Ser Cys Val Ser Thr His
            260                 265                 270

Thr Ala Asn Phe Gly Gln Gln Gly Ala Cys Glu Gly Val Leu Leu Leu
        275                 280                 285

Thr Leu Glu Glu Lys Thr Phe Pro Glu Asp Met Cys Tyr Pro Asp Gln
    290                 295                 300

Gly Gly Val Cys Gln Gly Thr Cys Val Gly Gly Gly Pro Tyr Ala Gln
```

-continued

```
              305                 310                 315                 320

Gly Glu Asp Ala Arg Met Leu Ser Leu Val Ser Lys Thr Glu Ile Glu
                325                 330                 335

Glu Asp Ser Phe Arg Gln Met Pro Thr Glu Asp Glu Tyr Met Asp Arg
            340                 345                 350

Pro Ser Gln Pro Thr Asp Gln Leu Leu Phe Leu Thr Glu Pro Gly Ser
        355                 360                 365

Lys Ser Thr Pro Pro Phe Ser Glu Pro Leu Glu Val Gly Glu Asn Asp
    370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
                405                 410                 415

Ser Ser Glu Asn Tyr Leu Gln Lys Glu Val Asp Ser Gly His Cys Pro
            420                 425                 430

His Trp Ala Ala Ser Pro Ser Pro Asn Trp Ala Asp Val Cys Thr Gly
        435                 440                 445

Cys Arg Asn Pro Pro Gly Glu Asp Cys Glu Pro Leu Val Gly Ser Pro
    450                 455                 460

Lys Arg Gly Pro Leu Pro Gln Cys Ala Tyr Gly Met Gly Leu Pro Pro
465                 470                 475                 480

Glu Glu Glu Ala Ser Arg Thr Glu Ala Arg Asp Gln Pro Glu Asp Gly
                485                 490                 495

Ala Asp Gly Arg Leu Pro Ser Ser Ala Arg Ala Gly Ala Gly Ser Gly
            500                 505                 510

Ser Ser Pro Gly Gly Gln Ser Pro Ala Ser Gly Asn Val Thr Gly Asn
        515                 520                 525

Ser Asn Ser Thr Phe Ile Ser Ser Gly Gln Val Met Asn Phe Lys Gly
    530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Glu Thr Leu Ala
                565                 570                 575

Arg Arg Asp Ser Phe Ala Gly Asn Gly Pro Arg Phe Pro Asp Pro Cys
            580                 585                 590

Gly Gly Pro Glu Gly Leu Arg Glu Pro Glu Lys Ala Ser Arg Pro Val
        595                 600                 605

Gln Glu Gln Gly Gly Ala Lys Ala
    610                 615

<210> SEQ ID NO 3
<211> LENGTH: 232
<212> TYPE: PRT
<213> ORGANISM: Homo sapiens
<220> FEATURE:
<221> NAME/KEY: PEPTIDE
<222> LOCATION: (1)..(232)
<223> OTHER INFORMATION:

<400> SEQUENCE: 3

Glu Pro Arg Ser Cys Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45
```

```
Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Asp Tyr Lys Cys Lys Val Ser Asn Lys Ala
            100                 105                 110

Leu Pro Ala Pro Met Gln Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Arg
145                 150                 155                 160

His Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 4
<211> LENGTH: 1878
<212> TYPE: DNA
<213> ORGANISM: Murine
<220> FEATURE:
<221> NAME/KEY: CDS
<222> LOCATION: (1)..(1875)
<223> OTHER INFORMATION:

<400> SEQUENCE: 4 atg gcc ccg cgc gcc cgg cgg cgc cgc cag ctg ccc gcg ccg ctg ctg    48
Met Ala Pro Arg Ala Arg Arg Arg Arg Gln Leu Pro Ala Pro Leu Leu
1               5                   10                  15 gcg ctc tgc gtg ctg ctc gtt cca ctg cag gtg act ctc cag gtc act    96
Ala Leu Cys Val Leu Leu Val Pro Leu Gln Val Thr Leu Gln Val Thr
                20                  25                  30 cct cca tgc acc cag gag agg cat tat gag cat ctc gga cgg tgt tgc   144
Pro Pro Cys Thr Gln Glu Arg His Tyr Glu His Leu Gly Arg Cys Cys
            35                  40                  45 agc aga tgc gaa cca gga aag tac ctg tcc tct aag tgc act cct acc   192
Ser Arg Cys Glu Pro Gly Lys Tyr Leu Ser Ser Lys Cys Thr Pro Thr
        50                  55                  60 tcc gac agt gtg tgt ctg ccc tgt ggc ccc gat gag tac ttg gac acc   240
Ser Asp Ser Val Cys Leu Pro Cys Gly Pro Asp Glu Tyr Leu Asp Thr
65                  70                  75                  80 tgg aat gaa gaa gat aaa tgc ttg ctg cat aaa gtc tgt gat gca ggc   288
Trp Asn Glu Glu Asp Lys Cys Leu Leu His Lys Val Cys Asp Ala Gly
                85                  90                  95 aag gcc ctg gtg gcg gtg gat cct ggc aac cac acg gcc ccg cgt cgc   336
Lys Ala Leu Val Ala Val Asp Pro Gly Asn His Thr Ala Pro Arg Arg
            100                 105                 110 tgt gct tgc acg gct ggc tac cac tgg aac tca gac tgc gag tgc tgc   384
Cys Ala Cys Thr Ala Gly Tyr His Trp Asn Ser Asp Cys Glu Cys Cys
```

```
                                                -continued
            115                 120                 125
cgc agg aac acg gag tgt gca cct ggc ttc gga gct cag cat ccc ttg      432
Arg Arg Asn Thr Glu Cys Ala Pro Gly Phe Gly Ala Gln His Pro Leu
        130                 135                 140 cag ctc aac aag gat acg gtg tgc aca ccc tgc ctc ctg ggc ttc ttc      480
Gln Leu Asn Lys Asp Thr Val Cys Thr Pro Cys Leu Leu Gly Phe Phe
145                 150                 155                 160 tca gat gtc ttt tcg tcc aca gac aaa tgc aaa cct tgg acc aac tgc      528
Ser Asp Val Phe Ser Ser Thr Asp Lys Cys Lys Pro Trp Thr Asn Cys
                165                 170                 175 acc ctc ctt gga aag cta gaa gca cac cag ggg aca acg gaa tca gat      576
Thr Leu Leu Gly Lys Leu Glu Ala His Gln Gly Thr Thr Glu Ser Asp
            180                 185                 190 gtg gtc tgc agc tct tcc atg aca ctg agg aga cca ccc aag gag gcc      624
Val Val Cys Ser Ser Ser Met Thr Leu Arg Arg Pro Pro Lys Glu Ala
                195                 200                 205 cag gct tac ctg ccc agt ctc atc gtt ctg ctc ctc ttc atc tct gtg      672
Gln Ala Tyr Leu Pro Ser Leu Ile Val Leu Leu Leu Phe Ile Ser Val
    210                 215                 220 gta gta gtg gct gcc atc atc ttc ggc gtt tac tac agg aag gga ggg      720
Val Val Val Ala Ala Ile Ile Phe Gly Val Tyr Tyr Arg Lys Gly Gly
225                 230                 235                 240 aaa gcg ctg aca gct aat ttg tgg aat tgg gtc aat gat gct tgc agt      768
Lys Ala Leu Thr Ala Asn Leu Trp Asn Trp Val Asn Asp Ala Cys Ser
                245                 250                 255 agt cta agt gga aat aag gag tcc tca ggg gac cgt tgt gct ggt tcc      816
Ser Leu Ser Gly Asn Lys Glu Ser Ser Gly Asp Arg Cys Ala Gly Ser
            260                 265                 270 cac tcg gca acc tcc agt cag caa gaa gtg tgt gaa ggt atc tta cta      864
His Ser Ala Thr Ser Ser Gln Gln Glu Val Cys Glu Gly Ile Leu Leu
        275                 280                 285 atg act cgg gag gag aag atg gtt cca gaa gac ggt gct gga gtc tgt      912
Met Thr Arg Glu Glu Lys Met Val Pro Glu Asp Gly Ala Gly Val Cys
    290                 295                 300 ggg cct gtg tgt gcg gca ggt ggg ccc tgg gca gaa gtc aga gat tct      960
Gly Pro Val Cys Ala Ala Gly Gly Pro Trp Ala Glu Val Arg Asp Ser
305                 310                 315                 320 agg acg ttc aca ctg gtc agc gag gtt gag acg caa gga gac ctc tcg     1008
Arg Thr Phe Thr Leu Val Ser Glu Val Glu Thr Gln Gly Asp Leu Ser
                325                 330                 335 agg aag att ccc aca gag gat gag tac acg gac cgg ccc tcg cag cct     1056
Arg Lys Ile Pro Thr Glu Asp Glu Tyr Thr Asp Arg Pro Ser Gln Pro
            340                 345                 350 tcg act ggt tca ctg ctc cta atc cag cag gga agc aaa tct ata ccc     1104
Ser Thr Gly Ser Leu Leu Leu Ile Gln Gln Gly Ser Lys Ser Ile Pro
        355                 360                 365 cca ttc cag gag ccc ctg gaa gtg ggg gag aac gac agt tta agc cag     1152
Pro Phe Gln Glu Pro Leu Glu Val Gly Glu Asn Asp Ser Leu Ser Gln
    370                 375                 380 tgt ttc acc ggg act gaa agc acg gtg gat tct gag ggc tgt gac ttc     1200
Cys Phe Thr Gly Thr Glu Ser Thr Val Asp Ser Glu Gly Cys Asp Phe
385                 390                 395                 400 act gag cct ccg agc aga act gac tct atg ccc gtg tcc cct gaa aag     1248
Thr Glu Pro Pro Ser Arg Thr Asp Ser Met Pro Val Ser Pro Glu Lys
                405                 410                 415 cac ctg aca aaa gaa ata gaa ggt gac agt tgc ctc ccc tgg gtg gtc     1296
His Leu Thr Lys Glu Ile Glu Gly Asp Ser Cys Leu Pro Trp Val Val
            420                 425                 430 agc tcc aac tca aca gat ggc tac aca ggc agt ggg aac act cct ggg     1344
Ser Ser Asn Ser Thr Asp Gly Tyr Thr Gly Ser Gly Asn Thr Pro Gly
```

```
                Ser Ser Asn Ser Thr Asp Gly Tyr Thr Gly Ser Gly Asn Thr Pro Gly
                        435                 440                 445 gag gac cat gaa ccc ttt cca ggg tcc ctg aaa tgt gga cca ttg ccc       1392
Glu Asp His Glu Pro Phe Pro Gly Ser Leu Lys Cys Gly Pro Leu Pro
        450                 455                 460 cag tgt gcc tac agc atg ggc ttt ccc agt gaa gca gca gcc agc atg       1440
Gln Cys Ala Tyr Ser Met Gly Phe Pro Ser Glu Ala Ala Ala Ser Met
465                 470                 475                 480 gca gag gcg gga gta cgg ccc cag gac agg gct gat gag agg gga gcc       1488
Ala Glu Ala Gly Val Arg Pro Gln Asp Arg Ala Asp Glu Arg Gly Ala
                485                 490                 495 tca ggg tcc ggg agc tcc ccc agt gac cag cca cct gcc tct ggg aac       1536
Ser Gly Ser Gly Ser Ser Pro Ser Asp Gln Pro Pro Ala Ser Gly Asn
            500                 505                 510 gtg act gga aac agt aac tcc acg ttc atc tct agc ggg cag gtg atg       1584
Val Thr Gly Asn Ser Asn Ser Thr Phe Ile Ser Ser Gly Gln Val Met
        515                 520                 525 aac ttc aag ggt gac atc atc gtg gtg tat gtc agc cag acc tcg cag       1632
Asn Phe Lys Gly Asp Ile Ile Val Val Tyr Val Ser Gln Thr Ser Gln
    530                 535                 540 gag ggc ccg ggt tcc gca gag ccc gag tcg gag ccc gtg ggc cgc cct       1680
Glu Gly Pro Gly Ser Ala Glu Pro Glu Ser Glu Pro Val Gly Arg Pro
545                 550                 555                 560 gtg cag gag gag acg ctg gca cac aga gac tcc ttt gcg ggc acc gcg       1728
Val Gln Glu Glu Thr Leu Ala His Arg Asp Ser Phe Ala Gly Thr Ala
                565                 570                 575 ccg cgc ttc ccc gac gtc tgt gcc acc ggg gct ggg ctg cag gag cag       1776
Pro Arg Phe Pro Asp Val Cys Ala Thr Gly Ala Gly Leu Gln Glu Gln
            580                 585                 590 ggg gca ccc cgg cag aag gac ggg aca tcg cgg ccg gtg cag gag cag       1824
Gly Ala Pro Arg Gln Lys Asp Gly Thr Ser Arg Pro Val Gln Glu Gln
        595                 600                 605 ggt ggg gcg cag act tca ctc cat acc cag ggg tcc gga caa tgt gca       1872
Gly Gly Ala Gln Thr Ser Leu His Thr Gln Gly Ser Gly Gln Cys Ala
    610                 615                 620 gaa tga                                                                1878
Glu
625

<210> SEQ ID NO 5
<211> LENGTH: 625
<212> TYPE: PRT
<213> ORGANISM: Murine

<400> SEQUENCE: 5

Met Ala Pro Arg Ala Arg Arg Arg Gln Leu Pro Ala Pro Leu Leu
1               5                   10                  15

Ala Leu Cys Val Leu Leu Val Pro Leu Gln Val Thr Leu Gln Val Thr
                20                  25                  30

Pro Pro Cys Thr Gln Glu Arg His Tyr Glu His Leu Gly Arg Cys Cys
            35                  40                  45

Ser Arg Cys Glu Pro Gly Lys Tyr Leu Ser Ser Lys Cys Thr Pro Thr
        50                  55                  60

Ser Asp Ser Val Cys Leu Pro Cys Gly Pro Asp Glu Tyr Leu Asp Thr
65                  70                  75                  80

Trp Asn Glu Glu Asp Lys Cys Leu Leu His Lys Val Cys Asp Ala Gly
                85                  90                  95

Lys Ala Leu Val Ala Val Asp Pro Gly Asn His Thr Ala Pro Arg Arg
                100                 105                 110
```

```
Cys Ala Cys Thr Ala Gly Tyr His Trp Asn Ser Asp Cys Glu Cys Cys
        115                 120                 125
Arg Arg Asn Thr Glu Cys Ala Pro Gly Phe Gly Ala Gln His Pro Leu
        130                 135                 140
Gln Leu Asn Lys Asp Thr Val Cys Thr Pro Cys Leu Leu Gly Phe Phe
145                 150                 155                 160
Ser Asp Val Phe Ser Ser Thr Asp Lys Cys Lys Pro Trp Thr Asn Cys
                165                 170                 175
Thr Leu Leu Gly Lys Leu Glu Ala His Gln Gly Thr Thr Glu Ser Asp
                180                 185                 190
Val Val Cys Ser Ser Ser Met Thr Leu Arg Arg Pro Lys Glu Ala
                195                 200                 205
Gln Ala Tyr Leu Pro Ser Leu Ile Val Leu Leu Phe Ile Ser Val
        210                 215                 220
Val Val Val Ala Ala Ile Ile Phe Gly Val Tyr Tyr Arg Lys Gly Gly
225                 230                 235                 240
Lys Ala Leu Thr Ala Asn Leu Trp Asn Trp Val Asn Asp Ala Cys Ser
                245                 250                 255
Ser Leu Ser Gly Asn Lys Glu Ser Ser Gly Asp Arg Cys Ala Gly Ser
                260                 265                 270
His Ser Ala Thr Ser Ser Gln Gln Glu Val Cys Glu Gly Ile Leu Leu
        275                 280                 285
Met Thr Arg Glu Glu Lys Met Val Pro Glu Asp Gly Ala Gly Val Cys
        290                 295                 300
Gly Pro Val Cys Ala Ala Gly Gly Pro Trp Ala Glu Val Arg Asp Ser
305                 310                 315                 320
Arg Thr Phe Thr Leu Val Ser Glu Val Glu Thr Gln Gly Asp Leu Ser
                325                 330                 335
Arg Lys Ile Pro Thr Glu Asp Glu Tyr Thr Asp Arg Pro Ser Gln Pro
                340                 345                 350
Ser Thr Gly Ser Leu Leu Leu Ile Gln Gln Gly Ser Lys Ser Ile Pro
        355                 360                 365
Pro Phe Gln Glu Pro Leu Glu Val Gly Glu Asn Asp Ser Leu Ser Gln
        370                 375                 380
Cys Phe Thr Gly Thr Glu Ser Thr Val Asp Ser Glu Gly Cys Asp Phe
385                 390                 395                 400
Thr Glu Pro Pro Ser Arg Thr Asp Ser Met Pro Val Ser Pro Glu Lys
                405                 410                 415
His Leu Thr Lys Glu Ile Glu Gly Asp Ser Cys Leu Pro Trp Val Val
                420                 425                 430
Ser Ser Asn Ser Thr Asp Gly Tyr Thr Gly Ser Gly Asn Thr Pro Gly
        435                 440                 445
Glu Asp His Glu Pro Phe Pro Gly Ser Leu Lys Cys Gly Pro Leu Pro
        450                 455                 460
Gln Cys Ala Tyr Ser Met Gly Phe Pro Ser Glu Ala Ala Ala Ser Met
465                 470                 475                 480
Ala Glu Ala Gly Val Arg Pro Gln Asp Arg Ala Asp Glu Arg Gly Ala
                485                 490                 495
Ser Gly Ser Gly Ser Ser Pro Ser Asp Gln Pro Pro Ala Ser Gly Asn
                500                 505                 510
Val Thr Gly Asn Ser Asn Ser Thr Phe Ile Ser Ser Gly Gln Val Met
        515                 520                 525
```

```
Asn Phe Lys Gly Asp Ile Ile Val Val Tyr Val Ser Gln Thr Ser Gln
            530                 535                 540

Glu Gly Pro Gly Ser Ala Glu Pro Glu Ser Glu Pro Val Gly Arg Pro
545                 550                 555                 560

Val Gln Glu Glu Thr Leu Ala His Arg Asp Ser Phe Ala Gly Thr Ala
                565                 570                 575

Pro Arg Phe Pro Asp Val Cys Ala Thr Gly Ala Gly Leu Gln Glu Gln
            580                 585                 590

Gly Ala Pro Arg Gln Lys Asp Gly Thr Ser Arg Pro Val Gln Glu Gln
            595                 600                 605

Gly Gly Ala Gln Thr Ser Leu His Thr Gln Gly Ser Gly Gln Cys Ala
            610                 615                 620

Glu
625

<210> SEQ ID NO 6
<211> LENGTH: 33
<212> TYPE: PRT
<213> ORGANISM: Artificial Sequence
<220> FEATURE:
<223> OTHER INFORMATION: Murine

<400> SEQUENCE: 6

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
                20                  25                  30

Arg

<210> SEQ ID NO 7
<211> LENGTH: 954
<212> TYPE: DNA
<213> ORGANISM: Homo sapiens;
<220> FEATURE:
<221> NAME/KEY: CDS
<222> LOCATION: (1)..(951)
<223> OTHER INFORMATION:

<400> SEQUENCE: 7 atg cgc cgc gcc agc aga gac tac acc aag tac ctg cgt ggc tcg gag    48
Met Arg Arg Ala Ser Arg Asp Tyr Thr Lys Tyr Leu Arg Gly Ser Glu
1               5                   10                  15 gag atg ggc ggc ggc ccc gga gcc ccg cac gag ggc ccc ctg cac gcc    96
Glu Met Gly Gly Gly Pro Gly Ala Pro His Glu Gly Pro Leu His Ala
                20                  25                  30 ccg ccg ccg cct gcg ccg cac cag ccc ccc gcc gcc tcc cgc tcc atg   144
Pro Pro Pro Pro Ala Pro His Gln Pro Pro Ala Ala Ser Arg Ser Met
            35                  40                  45 ttc gtg gcc ctc ctg ggg ctg ggg ctg ggc cag gtt gtc tgc agc gtc   192
Phe Val Ala Leu Leu Gly Leu Gly Leu Gly Gln Val Val Cys Ser Val
        50                  55                  60 gcc ctg ttc ttc tat ttc aga gcg cag atg gat cct aat aga ata tca   240
Ala Leu Phe Phe Tyr Phe Arg Ala Gln Met Asp Pro Asn Arg Ile Ser
65                  70                  75                  80 gaa gat ggc act cac tgc att tat aga att ttg aga ctc cat gaa aat   288
Glu Asp Gly Thr His Cys Ile Tyr Arg Ile Leu Arg Leu His Glu Asn
                85                  90                  95 gca gat ttt caa gac aca act ctg gag agt caa gat aca aaa tta ata   336
Ala Asp Phe Gln Asp Thr Thr Leu Glu Ser Gln Asp Thr Lys Leu Ile
                100                 105                 110
```

```
cct gat tca tgt agg aga att aaa cag gcc ttt caa gga gct gtg caa     384
Pro Asp Ser Cys Arg Arg Ile Lys Gln Ala Phe Gln Gly Ala Val Gln
        115                 120                 125 aag gaa tta caa cat atc gtt gga tca cag cac atc aga gca gag aaa     432
Lys Glu Leu Gln His Ile Val Gly Ser Gln His Ile Arg Ala Glu Lys
    130                 135                 140 gcg atg gtg gat ggc tca tgg tta gat ctg gcc aag agg agc aag ctt     480
Ala Met Val Asp Gly Ser Trp Leu Asp Leu Ala Lys Arg Ser Lys Leu
145                 150                 155                 160 gaa gct cag cct ttt gct cat ctc act att aat gcc acc gac atc cca     528
Glu Ala Gln Pro Phe Ala His Leu Thr Ile Asn Ala Thr Asp Ile Pro
                165                 170                 175 tct ggt tcc cat aaa gtg agt ctg tcc tct tgg tac cat gat cgg ggt     576
Ser Gly Ser His Lys Val Ser Leu Ser Ser Trp Tyr His Asp Arg Gly
            180                 185                 190 tgg gcc aag atc tcc aac atg act ttt agc aat gga aaa cta ata gtt     624
Trp Ala Lys Ile Ser Asn Met Thr Phe Ser Asn Gly Lys Leu Ile Val
        195                 200                 205 aat cag gat ggc ttt tat tac ctg tat gcc aac att tgc ttt cga cat     672
Asn Gln Asp Gly Phe Tyr Tyr Leu Tyr Ala Asn Ile Cys Phe Arg His
    210                 215                 220 cat gaa act tca gga gac cta gct aca gag tat ctt caa cta atg gtg     720
His Glu Thr Ser Gly Asp Leu Ala Thr Glu Tyr Leu Gln Leu Met Val
225                 230                 235                 240 tac gtc act aaa acc agc atc aaa atc cca agt tct cat acc ctg atg     768
Tyr Val Thr Lys Thr Ser Ile Lys Ile Pro Ser Ser His Thr Leu Met
                245                 250                 255 aaa gga gga agc acc aag tat tgg tca ggg aat tct gaa ttc cat ttt     816
Lys Gly Gly Ser Thr Lys Tyr Trp Ser Gly Asn Ser Glu Phe His Phe
            260                 265                 270 tat tcc ata aac gtt ggt gga ttt ttt aag tta cgg tct gga gag gaa     864
Tyr Ser Ile Asn Val Gly Gly Phe Phe Lys Leu Arg Ser Gly Glu Glu
        275                 280                 285 atc agc atc gag gtc tcc aac ccc tcc tta ctg gat ccg gat cag gat     912
Ile Ser Ile Glu Val Ser Asn Pro Ser Leu Leu Asp Pro Asp Gln Asp
    290                 295                 300 gca aca tac ttt ggg gct ttt aaa gtt cga gat ata gat tga             954
Ala Thr Tyr Phe Gly Ala Phe Lys Val Arg Asp Ile Asp
305                 310                 315

<210> SEQ ID NO 8
<211> LENGTH: 317
<212> TYPE: PRT
<213> ORGANISM: Homo sapiens;

<400> SEQUENCE: 8

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
```

-continued

```
                    100             105             110
Pro Asp Ser Cys Arg Arg Ile Lys Gln Ala Phe Gln Gly Ala Val Gln
        115             120             125

Lys Glu Leu Gln His Ile Val Gly Ser Gln His Ile Arg Ala Glu Lys
        130             135             140

Ala Met Val Asp Gly Ser Trp Leu Asp Leu Ala Lys Arg Ser Lys Leu
145             150             155             160

Glu Ala Gln Pro Phe Ala His Leu Thr Ile Asn Ala Thr Asp Ile Pro
                165             170             175

Ser Gly Ser His Lys Val Ser Leu Ser Ser Trp Tyr His Asp Arg Gly
            180             185             190

Trp Ala Lys Ile Ser Asn Met Thr Phe Ser Asn Gly Lys Leu Ile Val
        195             200             205

Asn Gln Asp Gly Phe Tyr Tyr Leu Tyr Ala Asn Ile Cys Phe Arg His
        210             215             220

His Glu Thr Ser Gly Asp Leu Ala Thr Glu Tyr Leu Gln Leu Met Val
225             230             235             240

Tyr Val Thr Lys Thr Ser Ile Lys Ile Pro Ser Ser His Thr Leu Met
            245             250             255

Lys Gly Gly Ser Thr Lys Tyr Trp Ser Gly Asn Ser Glu Phe His Phe
                260             265             270

Tyr Ser Ile Asn Val Gly Gly Phe Phe Lys Leu Arg Ser Gly Glu Glu
        275             280             285

Ile Ser Ile Glu Val Ser Asn Pro Ser Leu Leu Asp Pro Asp Gln Asp
        290             295             300

Ala Thr Tyr Phe Gly Ala Phe Lys Val Arg Asp Ile Asp
305             310             315
```